United States Patent
Taylor

(12) 
(10) Patent No.: US 6,500,827 B2
(45) Date of Patent: Dec. 31, 2002

(54) DRUG COMBINATIONS

(75) Inventor: Duncan Paul Taylor, Kalamazoo, MI (US)

(73) Assignee: Pharmacia & Upjohn Company, Kalamazoo, MI (US)

(*) Notice: Subject to any disclaimer, the term of this patent is extended or adjusted under 35 U.S.C. 154(b) by 56 days.

(21) Appl. No.: 09/987,774

(22) Filed: Jul. 11, 2001

(65) Prior Publication Data

US 2002/0040041 A1 Apr. 4, 2002

Related U.S. Application Data

(63) Continuation of application No. 09/674,380, filed as application No. PCT/US99/06523 on Apr. 14, 1999, now abandoned.
(60) Provisional application No. 60/084,860, filed on May 8, 1998.

(51) Int. Cl.[7] ............... A61K 31/535; A61K 31/50; A61K 31/495
(52) U.S. Cl. ............... 514/239.2; 514/236.2; 514/247; 514/249
(58) Field of Search ............... 514/239.2, 247, 514/236.2, 249

(56) References Cited

U.S. PATENT DOCUMENTS

| | | | | |
|---|---|---|---|---|
| 4,229,449 A | * | 10/1980 | Melloni et al. | 424/248.58 |
| 5,525,347 A | * | 6/1996 | Kellner et al. | 424/408 |
| 5,532,268 A | * | 7/1996 | Wong et al. | 514/432 |
| 5,798,393 A | * | 8/1998 | Swartz | 514/652 |
| 6,028,070 A | * | 2/2000 | Helligenstein | 514/239.2 |
| 6,046,193 A | * | 4/2000 | Helligenstein | 514/239.2 |
| 6,184,222 B1 | * | 2/2001 | Helligenstein | 514/239.2 |

OTHER PUBLICATIONS

"Pindolol induces a rapid improvement of depressed patients treated with serotonin reuptake inhibitors", Artigas et al., 1994, Arch Gen Psychiatry.*

* cited by examiner

*Primary Examiner*—Zohreh Fay
*Assistant Examiner*—Brian-Yong S. Kwon
(74) *Attorney, Agent, or Firm*—Stephen L. Nesbitt

(57) ABSTRACT

This patent application describes a new combination treatment of selective, noradrenaline-reuptake inhibitors (NARI) and specifically, reboxetine, and pindolol to provide rapid relief to patients suffering from depression, general anxiety, attention deficit hyperactivity disorder (ADHD), anxiety disorders such as obsessive compulsive disorders (OCD), panic disorders (PD), social phobia (SD) and the like.

10 Claims, No Drawings

DRUG COMBINATIONS

This application is a continuation of Ser. No. 09/674,380 filed Oct. 11, 2000 which is a 371 of PCT/US99/00623 filed Apr. 14, 1999, now abandoned which claim benefit of Ser. No. 60/084,860 filed May 8, 1998.

FIELD OF THE INVENTION

This invention describes new treatments that should provide for a fast acting rapid onset of relief from several nervous system disorders, and it involves the administration of the drug reboxetine in combination with the drug pindolol.

BACKGROUND

The introduction of tricyclic antidepressants in the early 1960s has provided a major advance in the treatment of neuropsychiatric disorders. Reactive and endogenous depressions, diagnoses formerly carrying grave prognostic implications, have become, with the introduction of the tricyclics, manageable disorders with a much smaller toll on the patient and the society as a whole.

The early tricyclic compounds were reuptake inhibitors of all the catecholamines released in the synaptic cleft, thus resulting in prolongation and enhancement of the dopamine (DA), noradrenaline (NA) and serotonin (5-hydroxytryptamine=5-HT) action. Lack of selectivity also causes undesired side effects particularly on the acetylcholine (especially the muscarinic component), and histamine mediated neurotransmission.

Because of these unwanted pharmacodynamic activities, cognitive impairment, sedation, urinary and gastrointestinal tract disturbances, increased intraocular pressure were limiting factors in the clinical use of these compounds and often required discontinuation of treatment. Of utmost concern were also the cardiac toxic effects and the proconvulsant activity of this group of drugs.

More recently, selective reuptake inhibitors for serotonin (SSRI) have been introduced with definite advantages in regard to fewer side effects without loss of efficacy.

SUMMARY OF THE INVENTION

Here we present the surprising finding that when the drug pindolol is given to a patient concurrently with a drug from a new category of antidepressants, a so called noradrenaline (NA) reuptake inhibitor (NARI), the combination of drugs act with surprising speed in relieving the symptoms of depression and it may be used for treating the symptoms of other central nervous system disorders including, but not only, general anxiety, Addictive Disorders, attention deficit hyperactivity disorder (ADHD), anxiety disorders such as obsessive compulsive disorders (OCD), panic disorders (PD), social phobia (SP) and the like.

One particular NARI that is preferred is reboxetine. Reboxetine is the generic name of the pharmaceutical substance with the chemical name of 2-(I-((2-ethoxyphenoxy)benzyl)-morpholine, and its pharmaceutically acceptable salts. Reboxetine can be a free base, or it can include reboxetine methanesulfonate (also called reboxetine mesylate) or any other pharmaceutically acceptable salt that does not significantly affect the pharmaceutical activity of the substance.

The chemical name of pindolol is 1-(1H-Indol-4-yloxy)-3-[(1-methylethyl)amino]-2-propanol; 4-[2-hydroxy-3-(isopropylamino)-propoxy]indole; pinodolol. Pindolol is described in U.S. Pat. No. 3,471,515, incorporated by reference and process steps are described in Swiss patents 469,002 and 472,404, assigned to the Sandoz Company, now the Novartis company, all documents incorporated into this document by reference. It has the trade name VISKEN®.

The present invention provides for the dosing of both reboxetine and pindolol, concurrently. The dosages for reboxetine and pindolol can be measured separately. The two drugs can be given as a single combined dose or given separately. They may be given at the same or at different times as long as both drugs are in the patient at one time over a 24 hour period. The two drugs will preferably be given to the patient, concomitantly, concurrently, at or about the same time, within about 5, 10, or 30 minutes, or they may be given within 1, 2, 3, 4, 5, 6, 8, 10, 12, 18 or about 24 hours, or fractions of minutes or of hours of each other. Concomitant or concurrent administration means the patient takes one drug within about 5 minutes of taking the other drug. Because the goal here is to provide rapid symptomatic relief to the patient, in most cases when treatment is started the two drugs would be administered to the patient close in time and typically concomitantly; thereafter, the timing of each drug's administration may not be as important.

A preferred dose range of reboxetine is 4 to 10 mg per patient per day and the more preferred dose is 6 to 8 mg or 8 to 10 mg per patient daily, depending upon the patient, delivered twice a day (b.i.d.). The reboxetine should be given to a patient concurrently with pindolol.

A preferred dose range of pindolol is 10–60 mg per patient per day and the more preferred dose is about 10 mg per patient daily, depending upon the patient, delivered twice a day (b.i.d.). Preferably the pindolol should be given concurrently with reboxetine as described above.

ADDITIONAL DESCRIPTION OF THE INVENTION AND DESCRIPTION OF THE PREFERRED EMBODIMENT(S)

Reboxetine is the generic name of the pharmaceutical substance with the chemical name of 2-(I-((2-ethoxyphenoxy)benzyl)-morpholine, and its pharmaceutically acceptable salts. Reboxetine can be a free base, or it can include reboxetine methanesulfonate (also called reboxetine mesylate) or any other pharmaceutically acceptable salt that does not significantly affect the pharmaceutical activity of the substance. Reboxetine and a method of synthesis are described in U.S. Pat. No. 4,229,449, issued Oct. 21, 1980, Melloni et. al., incorporated by reference into this document, methods of preparation are described in U.S. Pat. No. 5,068,433, issued Nov. 26, 1991, Melloni et. al. and in U.S. Pat. No. 5,391,735, issued Feb. 21, 1995, both incorporated by reference. Reboxetine may also be known under the trade name of EDRONAX™.

The pharmaceutical compositions and methods of administration described in U.S. Pat. No. 4,229,449 at col. 18, lines 33–66 are specifically incorporated by reference. Twice a day dosing is preferred with current formulations.

Reboxetine acts as an antidepressant. Antidepressants are frequently grouped into categories or "generations." The first generation of antidepressants were usually tricyclic antidepressants such as maprotiline that affected various neurotransmitter systems and are associated with many undesirable side effects. The second generation of antidepressants, such as mianserine, mirtrazapine and trazodone are largely devoid of anticholinergic action and their adrenolytic and antihistaminic effects are weaker. These are contrasted with the third generation of antidepressants (e.g.

SSRI, ipsapirone, viloxazine, reboxetine, bupropione) that mediate only one of the three main neurotransmitter system for depression (5-HT, noradrenaline, dopamine) and they do not affect muscarine, histamine and adrenergic cerebral systems. Svestka, J. "Antidepressives of the 3rd, 4th and 5th generation," Cesk-Psychiatr. February 1994; 90(1):3–19. (Czech).

Reboxetine, however, does not act like most antidepressants. Unlike tricyclic antidepressants and even selective serotonin reuptake inhibitors (SSRIs), reboxetine is ineffective in the 8-OH-DPAT hypothermia test, indicating that reboxetine is not a selective serotonin reuptake inhibitor rather it is selective for the noradrenergic system. Thus, reboxetine is not an SSRI, rather it is considered a novel, selective, noradrenalinereuptake inhibitor (NARI). Leonard-BE, "Noradrenaline in basic models of depression." *European-Neuropsychopharnacol*. April 1997; 7 Suppl 1: S11–6; discussion S71–3. Unlike most drugs, reboxetine is a highly selective norepinephrine uptake inhibitor, with only marginal serotonin and no dopamine uptake inhibitory activity. The compound displays only weak or no anti-cholinergic activity in different animal models and is devoid of monoamine oxidase (MAO) inhibitory activity.

Reboxetine is highly potent and fast acting. Our investigations indicate reboxetine has potent antireserpine activity and combines the inhibitory properties of classical tricyclic antidepressants on the reuptake of noradrenaline with an ability to desensitize υ-adrenergic receptor function without showing any appreciable interaction with muscarinic cholinergic and I-adrenerigic receptors. Moreover, reboxetine shows less vagolytic activity than other tricyclic antidepressants.

In spite of the inherently fast action of reboxetine there is still a "lag" or delay from the time of administration of the drug until the time the drug provides symptomatic relief to the patient. The treatments described here decrease that lag time. A period of days and especially weeks between the administration of a drug and its effect in relieving depression can be devastating to a patient. The patient may conclude the drug is not effective and stop taking the drug, thus a quick onset of activity is critically important for treatments of this type. We have discovered that the combination of pinodolol and reboxetine provides highly effective relief of psychiatric disorders with a minimal delay in onset of activity.

Pindolol is the generic name for 1-(1H-Indol-4-yloxy)-3-[(1-methylethyl)amino]-2propanol; 4-[2-hydroxy-3-(isopropylamino)-propoxy]indole; prinodolol. Pindolol is described in U.S. Pat. No. 3,471,515, incorporated by reference and process steps are described in Swiss patents 469,002 and 472,404, assigned to the Sandoz Company, now the Novartis company, all documents incorporated into this document by reference. It has the trade name VISKEN®.

The dosage used to treat all of the disorders described here may be found above and below. Reboxetine is well tolerated and has a wide safety range, it can be administered in a dose range of active ingredient from about 1 to over 40 mg/kg. It is more commonly provided in dosages of from 1 to 20 mg per patient per day. Pindolol is also fairly safe although it is contraindicated for patients with bronchial asthmas, cardiac failure, heart block and severe bradycardia. Other adverse reactions are possible. Pindolol dosages in the range of 5 to 60 mg daily can be effective. Both compounds may be administered by any suitable method including a convenient oral dosage form. A preferred method is oral dosing twice a day. The preferred dose range of reboxetine is 4 to 20 and more preferably 4 to 10 mg per patient per day and the preferred dose range of pindolol is 10–20 mg per patient per day. When starting medication the more preferred dose of reboxetine is 6 to 8 mg or 8 to 10 mg and pindolol is 10 mg per patient daily, depending upon the patient, delivered twice a day (b.i.d.). It can also be given at dosages of 2, 4, 6, 8, 10 or 12 mg/patient per day or fractions thereof: For example, suitable administrations could be 4 mg of reboxetine and 5 mg of pindolol in the morning and 2 or 4 mg of Rebozetine and 5 mg of pindolol in the evening. A skilled practitioner would be expected to determine the precise level of dosing. The idea dosing would be routinely determined by an evaluation of the patient and the needs of the patient. This patent application describes the treatment of numerous conditions, disorders, diseases, and disease symptoms with the combination of drugs described herein, in addition to the conditions, disorders, diseases, and disease symptoms described above, the following may also be treated with these drugs: Addictive Disorders, Psychoactive Substance Use Disorders, Nicotine Addition or Tobacco Addiction (with a result of Smoking Cessation or a decrease in smoking) and Attention Deficit Hyperactivity Disorder (ADHD). This patent application also describes the treatment of Obsessive Compulsive Disorders (OCD), and Panic Disorder (PD), comprising administering a therapeutically effective, nontoxic dose of the drugs described herein and derivatives and or pharmaceutically acceptable salts thereof to a patient Addictive Disorders and Psychoactive Substance Use Disorders, such as Intoxication disorders, Inhalation disorders, Alcohol addiction, Tobacco Addiction and or Nicotine Addiction. Tobacco and Nicotine addiction would be treated with the goal of achieving either Smoking Cessation or Smoking Reductions.

Addictive Disorders, Alcohol and Other Psychoactive Substance Use Disorders, disorders related to Intoxication and Inhalants and especially Tobacco Addiction or Nicotine Addiction, may be treated with the drugs described herein. Tobacco Addiction or Nicotine Addiction would be treated with the drugs described herein in order to achieve smoking/chewing cessation or smoking/chewing reduction. General descriptions of Addictive Disorders, including disorders related to Intoxication and Inhalants and Tobacco Addiction or Nicotine Addiction may be found in many standard sources, such as, The American Psychiatric Press Textbook of Psychiatry, Second Edition, Edited by Robert E. Hales, Stuart C. Yudofsky, and John A. Talbott, copyright 1994, incorporated by reference, especially pp. 401 et. seq., section on "Nicotine" incorporated by reference. Another of many texts is the Manual of Psychiatric Therapeutics, Second Edition, edited by Richard I. Shader, incorporated by reference, especially pp. 85 from Chapter 11 (Hypnosis).

The treatment of Alcohol and Other Psychoactive Substance Use Disorders, such as disorders related to Intoxication and Inhalants and Tobacco Addiction or Nicotine Addiction but especially Tobacco Addiction involves the administration of the drugs described herein in a manner and form that provide a reduction in the symptoms of the disease. Tobacco Addiction or Nicotine Addiction in particular would be treated to achieve a reduction or cessation of smoking or chewing of nicotine containing materials by a patient. Cessation or a reduction in smoking or chewing of addictive or psychoactive substances involves the administration of the drugs described herein in a manner and form that provide a reduction in the symptoms of the disease, or with Tobacco or Nicotine with a reduction in the amount smoked or chewed. See the general description above for administration of Reboxetine.

Attention Deficit Hyperactivity Disorder (ADHD)

ADHD is a condition or disease state that may be treated with the drugs described herein. General descriptions of ADHD, may be found in many standard sources, such as, The American Psychiatric Press Textbook of Psychiatry, Second Edition, Edited by Robert E. Hales, Stuart C. Yudofsky, and John A. Talbott, copyright 1994, incorporated by reference, especially pp. 741 et. al., section on "ADHD," incorporated by reference. Another of many texts is the Manual of Psychiatric Therapeutics, Second Edition, edited by Richard I. Shader, incorporated by reference, especially Chapter 18, Attention-Deficit hyperactivity Disorder, and pp. 172 et. seq., incorporated by reference.

The treatment of Attention Deficit Hyperactivity Disorder in children and adults involves the administration of the drugs described herein in a manner and form that provide a reduction in the symptoms of the disease. A child or young adult may require a smaller dosage depending upon the size, age, condition of the patient. See general description above for administration of the drugs described herein.

Obsessive Compulsive Disorders (OCD)

Obsessive Compulsive Disorder is a condition or state of anxiety that may be treated with reboxetine. General descriptions of OCD, may be found in many standard sources, such as, The American Psychiatric Press Textbook of Psychiatry, Second Edition, Edited by Robert E. Hales, Stuart C. Yudofsky, and John A. Talbott, copyright 1994, incorporated by reference, especially the chapter on "Anxiety Disorders," incorporated by reference. Another of many texts is the Manual of Psychiatric Therapeutics, Second Edition, edited by Richard I. Shader, incorporated by reference, especially Chapter 5, Obsessions and Compulsions, more particularly, Section III of that chapter, "OCD" pp. 36 et. seq., incorporated by reference.

The treatment of Obsessive Compulsive Disorders (OCD) involves the administration of reboxetine in a manner and form that provide a reduction in the symptoms of the disease. See general description above for administration of reboxetine.

The following study shows the therapeutic effectiveness of using reboxetine in doses varying from 6 to 8 mg to treat OCD. This study is provided to illustrate the usefulness of using reboxetine as a treatment for OCD and the invention described herein should not be considered limited by this example.

In a trial involving 10 patients with a DSM-III-R diagnosis of Obsessive Compulsive Disorder who were all treated with reboxetine for a period of 3 to 4 weeks with the dose for the first week at 6 mg (4 mg in a.m. and 2 mg in p.m.) with the dose increasing in the second week to 8 mg (4 mg b.i.d.). At CGI last assessment, one patient was judged very much improved, 4 were judged much improved, 2 minimally improved, while 3 were unchanged. Of the patients who did respond they had a decrease of the obsessive-compulsive symptomatology, as measured by the CPRS-OC rating scale, of more than 30 and as much as 73%.

Panic Disorder (PD)

Panic Disorder is a condition or state of anxiety that may be treated with reboxetine. General descriptions of PD, may be found in many standard sources, such as, The American Psychiatric Press Textbook of Psychiatry, Second Edition, Edited by Robert E. Hales, Stuart C. Yudofsky, and John A. Talbott, copyright 1994, incorporated by reference, especially the chapter on "Anxiety Disorders," incorporated by reference, another of many texts is the Manual of Psychiatric Therapeutics, Second Edition, edited by Richard I. Shader, incorporated by reference, especially Chapter 25, "Approaches to the Treatment of Anxiety States," incorporated by reference.

The treatment of Panic Disorder involves the administration of the drugs described herein in a manner and form that provide a reduction in the symptoms of the disease. See general description above.

What is claimed is:

1. A method of treating a patient experiencing symptoms of general anxiety disorders (GADs), comprising the administration of a therapeutically effective, nontoxic dose of pindolol, its derivatives and or pharmaceutically acceptable salts thereof to a patient and administering a therapeutically effective, nontoxic dose of a selective, a noradrenaline reuptake inhibitor (NARI), its derivatives and or pharmaceutically acceptable salts thereof to a patient.

2. A method of treating a patient as in claim 1 where the noradrenaline reuptake inhibitor (NARI) is reboxetine.

3. A method of treating a patient as in claim 2 where the administration of the dose of pindolol is administered within 24 hours of the administration of the dose of reboxetine.

4. The method of claim 3 where the pindolol is administered within 12 hours of the reboxetine.

5. The method of claim 4 where the pindolol is administered within 6 hours of the reboxetine.

6. The method of claim 5 where the pindolol is administered within 3 hours of the reboxetine.

7. The method of claim 6 where the pindolol is administered within 1 hour of the reboxetine.

8. The method of claim 7 where the pindolol and reboxetine are administered concomitantly.

9. The method of any one of claims 1–8 where the reboxetine dose is from about 4 to 10 mg per patient per day and the pindolol dose range is from about 10 to 20 mg per patient per day, delivered twice a day.

10. The method of any one of claims 1–8 where the reboxetine dose is from about 6 to 8 mg per patient per day and the pindolol dose range is from about 10 to 16 mg per patient per day, delivered twice a day.

* * * * *